United States Patent [19]

Berke et al.

[11] Patent Number: 4,525,480

[45] Date of Patent: Jun. 25, 1985

[54] COMPOSITION OF MATTER CONTAINING CINNAMALDEHYDE AND PARABENS

[75] Inventors: Philip A. Berke, Madison; William E. Rosen, Summit, both of N.J.

[73] Assignee: Sutton Laboratories, Inc., Chatham, N.J.

[21] Appl. No.: 503,166

[22] Filed: Jun. 10, 1983

[51] Int. Cl.$^3$ ............................................. A01N 37/10
[52] U.S. Cl. ..................................... 514/544; 514/701
[58] Field of Search ..................... 424/308; 426/330.2, 426/335

[56] References Cited

U.S. PATENT DOCUMENTS 3,853,998 12/1974 Rubio ................................. 426/335
3,951,820 4/1976 Jurd et al. ......................... 426/335

OTHER PUBLICATIONS

"Milk Hygiene"; World Health Organization; (1962) pp. 7-15, 35-37, 55, 306-307, 309, 570-571, 574, 577-578 & 596.
Encyclopedia of Chemical Technology, Kirk-Othmer, 3rd Ed., (1981), vol. 15; 523-526 & 552-553.
Handbook of Food Additives, CRC (1968), pp. 417, & 428.
Cosmetics, Science and Technology, 2nd Edition, vol. 3, (1974), pp. 579-581.
Cosmetics, Science and Technology, 2nd Edition, vol. 1, (1974), p. 207.
Disinfection, Sterilization and Preservation; 2nd Edit. (1977), p. 772.
Lord et al., Chemical Abstracts vol. 48 (1954), 11730f.
Cosmetics; Science and Technology; Sagarin, pp. 1054-1059, (1957).
Earl L. Richardson, Cosmetics & Toiletries, vol. 96, Mar. 1981, "Update-Frequency of Preservative Use in Cosmetic Formulas as Disclosed to FDA", pp. 91, 92.
Cosmetics & Toiletries, vol. 97, No. 11, p. 57, Nov. 1982, Raymond L. Decker et al., "Frequency of Preservative Use in Cosmetic Formulas as Disclosed to FDA-1982, Update".
Encyclopedia of Chemical Technology, Third Ed., vol. 6, pp. 145-147, Kirk-Othmer.
U.S. Dispensatory, 27th Ed. (1973), Publ. J. B. Lippincott Co. pp. 319-320.
Official Monographs (1980), p. 1222.
Remington's Pharmaceutical Sciences, Mack Printing Co., (1980), Chapter 67, p. 1232.
U.S. Pharmacopeia XVI (1960), p. 164.
Merck Index, 9th Ed. (1976), p. 2291.

*Primary Examiner*—Leonard Schenkman
*Assistant Examiner*—Joseph A. Lipovsky
*Attorney, Agent, or Firm*—Bacon & Thomas

[57] ABSTRACT

A composition of matter comprised of cinnamaldehyde and one or more esters of p-hydroxybenzoic acid, commonly known as parabens, is disclosed. The composition exhibits synergistic activity against a wide range of microorganisms which contaminate ingestible products.

8 Claims, No Drawings

COMPOSITION OF MATTER CONTAINING CINNAMALDEHYDE AND PARABENS

BACKGROUND OF THE INVENTION

1. Technical Field of the Invention

This invention is directed to a synergistic combination of cinnamaldehyde and parabens for antimicrobial preservation of foods, pharmaceuticals, and cosmetics.

2. Description of the Prior Art

Cinnamaldehyde, also referred to as cinnamic aldehyde, is an unsaturated aromatic aldehyde prepared by condensing benzaldehyde and acetaldehyde in the presence of sodium or calcium hydroxide. See, *Merck Index* 9th Edition (1976). It is principally used in the flavor and perfume industries.

Parabens, i.e., esters of p-hydroxybenzoic acid, are well known as preservatives in the food, pharmaceutical and cosmetic industries. While the methyl and propyl esters are most commonly used, the butyl and benzyl esters have also been used.

SUMMARY OF THE INVENTION

We have discovered that the combination of cinnamaldehyde and parabens exhibit synergistic activity against microorganisms which can contaminate foodstuffs, cosmetics, and pharmaceutical products. Heretofore, many foods and pharmaceutical products were inadequately preserved because most of the known preservatives have not proved to be safe for human ingestion. Because cinnamaldehyde has been used as a flavoring agent in foods, it is generally regarded as safe for human ingestion. Similarly, methylparaben and propylparaben, i.e., the methyl and propyl esters of p-hydroxybenzoic acid, are permitted to be used in foods and other products which are ingested.

Our discovery of synergism between cinnamaldehyde and parabens represents an important advance in food and pharmaceutical preservation because parabens alone have proved to be inadequate for preserving ingested products such as antacids and aloe extract containing products. Combining the heretofore unused cinnamaldehyde as a preservative ingredient in synergistic combination with parabens, therefore, provides a superior preservative system. Moreover, the use of cinnamaldehyde as a preservative permits the use of less of the unpleasant tasting parabens which is an obvious advantage in the preservation of food and other ingestible products.

Our invention, therefore, is directed to a synergistic preservative composition comprised of cinnamaldehyde and one or more esters of p-hydroxybenzoic acid, preferably the methyl and propyl esters. This composition provides an effective means of protecting ingestible products from microbial contamination.

DETAILED DESCRIPTION OF THE PREFERRED EMBODIMENTS

The composition of the invention is formed by combining cinnamaldehyde with paraben or mixtures of parabens in a weight ratio of cinnamaldehyde to paraben (or mixture of parabens) of approximately 1:10 to 4:1. The composition is incorporated into products to be preserved in amounts up to about 1%, by weight. Of course, the precise effective amount for preservation is dependent upon the particular product being preserved.

In preparing the composition, the paraben component may be dissolved into the cinnamaldehyde or the paraben and cinnamaldehyde may be blended with a mutually compatible diluent such as propylene glycol.

The following examples illustrate the effectiveness of the synergistic composition of the invention against a wide range of microorganisms.

Example I shows that an aqueous solution of the combination of cinnamaldehyde and parabens (methylparaben:propylparaben, 5:1) is effective in killing microbial changes of *P. aeruginosa* (bacteria), *C. albicans* (yeast) and *A. niger* (mold).

EXAMPLE I

Antimicrobial effectiveness of cinnamaldehyde—paraben combination in water

The following procedure for measuring critical killing time was carried out using a gram-negative bacterium (*P. aeruginosa* ATCC 9027), a yeast (*C. albicans* ATCC 10231), and a mold (*A. niger* ATCC 16404).

Bacteria

A 24 hour A.O.A.C. broth culture was used for the test. 0.5 ml. of the 24 hour culture was added to a 4.5 ml. of the test sample and mixed thoroughly. The sample was then stored at 35° C. in a hot air incubator for the duration of the test. At pre-selected time intervals of 24, 48, and 72 hours, a loopful (0.1 ml.) of the sample was aseptically removed from the incubator and placed in A.O.A.C. broth with Letheen. The tubes containing the inoculated broth were incubated for 48 hours at 35° C. and then examined for microbial growth.

If the sample turned the medium cloudy on the initial subculture, the subculture was incubated for 24 hours at 35° C. and thereafter subcultured again into fresh medium and incubated for 48 hours at 35° C.

Yeast

The same procedure was used as for bacteria, except Sabourand Liquid Medium with Letheen was used in place of A.O.A.C. broth with Letheen.

Molds

The growth of a 7-10 day slant was washed off with 10 ml. of sterile saline. 0.5 ml. of this suspension was added to 4.5 ml. of the sample and mixed thoroughly. The sample was stored at room temperature for the duration of the test. At pre-selected time intervals, a loopful (0.1 ml.) was removed and placed into Sabourand Liquid Media with Letheen and incubated for 7 days at room temperature and then examined for microbial growth.

If the sample turned the medium cloudy on the initial subculture the subculture was incubated for 24 hours at room temperature. After the 24 hour incubation, the test tube was subcultured again into fresh medium and incubated for 7 days at room temperature.

The results of challenge testing a combination of 0.10% cinnamaldehyde plus 0.25% methylparaben plus 0.05% propylparaben in water solution were as follows:

| Species | ATCC Number | Subculture After Incubation Times (Days)* | | |
|---|---|---|---|---|
| | | 1 | 2 | 3 |
| *P. aeruginosa* | 9027 | 0 | 0 | 0 |
| *C. Albicans* | 10231 | 0 | 0 | 0 |

| Species | ATCC Number | Subculture After Incubation Times (Days)* | | |
|---|---|---|---|---|
| | | 1 | 2 | 3 |
| A. niger | 16404 | 0 | 0 | 0 |

*Code: + = growth, 0 = no growth

Example II is a study of microbial spoilage times for milk, and demonstrates the synergism of cinnamaldehyde and parabens (methylparaben-propylparaben, 4:1). Unpreserved milk or milk containing insufficient preservative (0.025% or 0.05% cinnamaldehyde or 0.05 or 0.10% parabens) spoiled within 1 day. The use of 0.10% cinnalamdehyde delayed spoilage slightly (to 2 days), and the use of 0.20% parabens delayed spoilage to 14 days. Combinations of cinnamaldehyde and parabens prevented microbial spoilage significantly longer than that expected from the activities of the separate ingredients. For example, whereas milk containing 0.025% or 0.05% cinnamaldehyde spoiled in 1 day (like the unpreserved control), and milk containing 0.05% or 0.10% paraben (methylparabenpropylparaben, 4:1) also spoiled in 1 dday, the milk containing a combination of 0.05% cinnamaldehyde and 0.10% paraben spoiled only after 11 days. Similarly, although milk containing 0.10% cinnamaldehyde spoiled in 2 days, and milk containing 0.20% paraben spoiled in 14 days, milk containing the combination of 0.10% cinnamaldehyde plus 0.20% paraben did not spoil even after 40 days. In fact milk containing either 0.025% or 0.05% cinnamaldehyde in combination with 0.20% paraben also did not spoil even after 40 days. Where milk containing 0.10% cinnamaldehyde spoiled in 2 days and milk containing 0.10% parabens spoiled in 1 day, the milk containing 0.10% cinnamaldehyde plus 0.10% paraben spoiled only after 36 days. Also, milk containing 0.10% cinnamaldehyde plus 0.05% paraben spoiled only after 11 days. Mose impressively, milk containing 0.05% cinnamaldehyde plus 0.05% paraben did not spoil until after 5 days, even though *double* the amount of either ingredient lasted only 1 or 2 days. These comparisons are listed in the table below.

| Milk spoilage times with preservatives alone and in combination (concentration (spoilage time)): | | |
|---|---|---|
| Cinnamaldehyde alone | Parabens alone | Combination Cinnamaldehyde + paraben |
| 0.05% (1 day) | 0.10% (1 day) | 0.05 + 0.10 (11 days) |
| 0.10% (2 days) | 0.20% (14 days) | 0.10 + 0.20 (>40 days) |
| 0.025% (1 day) | 0.20% (14 days) | 0.025 + 0.20 (>40 days) |
| 0.05% (1 day) | 0.20% (14 days) | 0.05 + 0.20 (>40 days) |
| 0.10% (2 days) | 0.10% (1 day) | 0.10 + 0.10 (36 days) |
| 0.10% (2 days) | 0.05% (1 day) | 0.10 + 0.05 (11 days) |
| 0.05% (1 day) | 0.05% (1 day) | 0.05 + 0.05 (5 days) |
| 0.10% (2 days) | 0.10% (1 day) | |

EXAMPLE II

Antimicrobial effectiveness of cinnamaldehyde—paraben combinations—preservation of milk The microbial spoilage of whole milk at room temperature was delayed or prevented by the incorporation of cinnamaldehyde—paraben combinations. The following series of tests was terminated after 40 days.

| Preservative added to whole milk | | time to spoilage (i.e., development of odor, color, curdling etc) |
|---|---|---|
| Cinnamaldehyde | methylparaben-propylparaben (4:1) | |
| None | None | 1 day |
| 0.0.25% | None | 1 day |
| 0.05% | None | 1 day |
| 0.10% | None | 2 days |
| None | 0.05% | 1 day |
| None | 0.10% | 1 day |
| None | 0.20% | 14 days |
| 0.05% | 0.05% | 5 days |
| 0.05% | 0.10% | 11 days |
| 0.10% | 0.05% | 11 days |
| 0.10% | 0.10% | 36 days |
| 0.10% | 0.20% | >40 days |
| 0.025% | 0.20% | >40 days |
| 0.05% | 0.20% | >40 days |

The tests results on preserving milk is clear proof of synergism between cinnamaldehyde and parabens. Whereas 0.10% cinnamaldehyde delayed milk spoilage only one day, and 0.10% parabens did not delay spoilage at all, half the amounts of each—i.e., 0.05% cinnamaldehyde plus 0.05% parabens—delayed milk spoilage for 4 days. Moreover, 0.10% cinnamaldehyde plus 0.10% parabens prevented spoilage for a test period of 36 days. Other combinations of cinnamaldehyde plus parabens (e.g. 0.05 plus 0.10, 0.10 plus 0.05, 0.025 plus 0.02, etc.) also show antimicrobial synergism.

Example III shows that the cinnamaldehyde—paraben combination system is effective in preserving whole egg, and Example IV shows it preserves aloe extract which is used as a drink and as a pharmaceutical and cosmetic ingredient. Example V shows that the cinnamaldehyde—paraben combination effectively preserves gastric antacid preparations.

EXAMPLE III

Antimicrobial efffectiveness of cinnalamdehyde—paraben combination—preservation of egg The microbial spoilage of whole egg at room temperature was delayed or prevented by the incorporation of a cinnamaldehyde—paraben combination. The following series of tests was terminated after 68 days.

| Preservative added to whole eggs | | Time to spoilage (i.e., development of odor, and/or color, thickened, separated, etc.) |
|---|---|---|
| Cinnamaldehyde | Methylparaben-propylparaben (4:1) | |
| None | None | 3 days |
| 0.025% | 0.025% | 4 days |
| 0.05% | 0.05% | 15 days |
| 0.10% | 0.10% | 49 days |
| 0.20% | 0.20% | 68 + days |

EXAMPLE IV

Antimicrobial effectiveness of cinnamaldehyde—paraben combinations—preservation of aloe extract Extracts of the aloe plant are used in foods, drinks, cosmetics, and pharmaceuticals, either as such or as an ingredient in a formulated product. Aloe extracts support vigorous microbial growth unless properly preserved. Challenge tests on aloe extract containing cinnamaldehyde or cinnamaldehyde—paraben combination showed that the cinnalamaldehyde—paraben combination preservative was superior.

| Preservative added to aloe extract | | Bacterial counts after 3 days | | |
|---|---|---|---|---|
| Cinnamaldehyde | Methylparaben-propylparaben (4:1) | P. aeruginosa | C. albicans | A. niger |
| 0.05% | None | 3.1 × 10⁷ | 10 | 10 |
| 0.05% | 0.1% | 10 | 10 | 10 |

EXAMPLE V

Antimicrobial effectiveness of cinnamaldehyde—paraben combination—preservation of gastric antacids.

Gastric antacids are drugs which on ingestion react with the hydrochloric acid of the gastric contents to lower the acidity. Two commercial antacids containing aluminum hydroxide and magnesium hydroxide, and one preparation containing aluminum hydroxide, magnesium hydroxide and simethicone, were challenge tested with *P aeruginosa* both without preservative and with added 0.08% cinnamaldehyde plus 0.044% methylparaben plus 0.012% propylparaben.

| Antacid | Preservative | Subculture after Incubation at 35° C. for 3 days |
|---|---|---|
| I | None | + |
| I | Cinnamaldehyde + parabens | 0 |
| II | None | + |
| II | Cinnamaldehyde + parabens | 0 |
| III | None | + |
| III | Cinnamaldehyde + parabens | 0 |

Code: + = growth, 0 = no growth

As shown by the foregoing tests, the combination of cinnamaldehyde and parabens provides effective preservation against bacteria, yeast, and mold and exhibits synergism. The composition, therefore, provides a highly effective method for preserving products susceptible to microbial contamination and particularly ingestible products such as foods and parmaceuticals.

While the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

We claim:

1. A preservative composition comprising cinnamaldehyde and at least one ester of p-hydroxybenzoic acid selected from the group consisting of methylparaben, propylparaben and mixtures thereof having antimicrobial activity in a weight ratio of about 1:8 to 2:1.

2. An ingestible product susceptible to microbial contamination containing an anti-microbial effective amount up to about 1% by weight of the composition of claim 1.

3. The product of claim 2, wherein said product is a pharmaceutical product.

4. The product of claim 2, wherein said product is a foodstuff.

5. The product of claim 4, wherein said foodstuff contains aloe extract.

6. The product of claim 3, wherein said pharmaceutical product is a gastric antacid.

7. A cosmetic product susceptible to microbial contamination containing an anti-microbial effective amount up to 1% by weight of the composition of claim 1.

8. The product of claim 7, wherein said cosmetic is a cream, lotion or shampoo.

* * * * *